United States Patent [19]

Bauman et al.

[11] Patent Number: 4,659,674
[45] Date of Patent: Apr. 21, 1987

[54] QUALITY CONTROL METHOD FOR CONTAINERS

[75] Inventors: Bernard D. Bauman, Coopersburg; Rajendra K. Mehta, Allentown, both of Pa.

[73] Assignee: Air Products and Chemicals, Inc., Allentown, Pa.

[21] Appl. No.: 536,604

[22] Filed: Sep. 28, 1983

[51] Int. Cl.[4] .................. G01N 15/08; G01N 33/44
[52] U.S. Cl. .......................... 436/5; 73/38; 436/85
[58] Field of Search .............. 436/5, 85, 3; 204/1 T; 73/38, 52, 432 V, 432 Z

[56] References Cited

U.S. PATENT DOCUMENTS

| | | | |
|---|---|---|---|
| 2,811,468 | 10/1957 | Joffre | 117/95 |
| 3,303,109 | 2/1967 | Just | 204/1 |
| 3,512,003 | 5/1970 | Berry et al. | 73/73 |
| 3,530,045 | 9/1970 | Alburger | 204/1 |
| 3,649,472 | 3/1972 | Morrissey et al. | 204/1 T |
| 3,862,284 | 1/1975 | Dixon et al. | 264/83 |
| 4,357,143 | 11/1982 | Scott | 204/1 T |
| 4,391,128 | 7/1983 | McWhorter | 73/38 |

OTHER PUBLICATIONS

Theobald, The Analyst, vol. 84, No. 1002, pp. 570–571, 1959.
Becker, Fachz. Lab., vol. 16, No. 3, pp. 209–215, 1972.
Estimation of the Effective Permeability of Thin Surface Layers Created by Exposure of Polyethylene to Fluorine, Polym. Eng. Sci., Aug. 1982, vol. 22, No. 12, pp. 738–746, Koros et al.
Chemical Abstract 90:136330y.
Chemical Abstract 77:35385w.
Chemical Abstract 81:50360k.
Plastics Technology, 6/79, pp. 61–64.
Plastics World, 7/83, pp. 30–33, 87.
Plastics & Rubber Processing, 3/79, pp. 10–16.
Modern Plastics, 11/77, pp. 34–37.
Allen et al., Aust. J. Appl. Sci., vol. 12, (1961), pp. 42–55.

Primary Examiner—Barry S. Richman
Assistant Examiner—Robert J. Hill, Jr.
Attorney, Agent, or Firm—Richard A. Dannells, Jr.; James C. Simmons; E. Eugene Innis

[57] ABSTRACT

A method is provided for determining the impermeability of a polymeric article to a fluid by the steps of:
  (a) allowing a permeant to diffuse through the polymeric article for a preselected period of time,
  (b) converting permeant, diffusing through the article, to an ion by a chemical reaction and
  (c) measuring the amount of ion formed quantitatively with an ion-selective electrode.

A method is further provided wherein a polymeric article is exposed to a permeant for a fixed period of time; removed from contact with the permeant; exposed to a chemical which will convert permeant, back-diffusing through the polymeric article, to an ion; and quantitatively measuring the amount of thus-formed ion with a ion-specific electrode.

7 Claims, 6 Drawing Figures

QUALITY CONTROL METHOD FOR CONTAINERS

DESCRIPTION

TECHNICAL FIELD

This invention relates to a quality control method for determining the degree of impermeability of articles made from thermoplastic polymers toward liquids or volatile materials. More particularly, it relates to a method for determining the extent to which articles such as containers have become impermeable toward hydrocarbon or other liquids.

BACKGROUND ART

The use of blow molded thermoplastic containers and other hollow articles has become commercially significant as disclosed, for example, in the article "Blow Molding: The Next Five Years," *Plastics Technology*, (June, 1979), pages 61-64. Blow molding is a process which makes possible construction of intricately shaped, lightweight, corrosion-resistant containers, which have high mechanical strength. Containers made from thermoplastic resins can be used for the storage of aqueous or highly polar liquids and, for this purpose, are essentially impervious to the substances stored therein. However, blow molded thermoplastic containers are not entirely satisfactory for the storage of relatively nonpolar organic liquids because the organic liquids can diffuse through the walls of the thermoplastic container at an unacceptably high rate.

It would be highly desirable to be able to use blow molded thermoplastic containers for safe and long-term storage of commercially significant nonpolar fluids, including gasoline and other liquid fuels, motor oils, hydrocarbon-based cleaning fluids or household solvents and oil-based paints containing hydrocarbon solvents. In presently available thermoplastic containers, diffusion of hydrocarbon solvents through the walls thereof often leads to an unacceptable loss of at least part of the solvent material contained therein. As a result, the properties of the stored materials, for example, oil-based paint, may change so drastically as to become useless. It will also be apparent that blow molded containers for hydrocarbon fluids, e.g. gasoline tanks, have met with marginal commercial acceptance owing to the loss of fuel therefrom. Diffusion of even small amounts of gasoline through the walls of a fuel container will contribute to air pollution.

In addition to the use of thermoplastic containers for hydrocarbon liquids, thermoplastic materials can be used to package a variety of other commercially significant materials. Polyethylene terephthalate (PET) is widely used in containers for carbonated beverages. Aqueous ammonia solutions and hypochlorite bleach solutions are commonly packaged in thermoplastic bottles. Oxygen-sensitive materials, such as meats, are packaged in thermoplastic films. It is contemplated that dilute acetic acid, i.e. vinegar, could be packaged in plastic materials, as well as home permanent waving solutions.

Thermoplastic resins which can be blow molded include polymers and copolymers of styrene, acrylonitrile, vinyl chloride and olefins containing at least one aliphatic mono-1-olefin having a maximum of 8 carbon atoms. Polyethylene terephthalate is representative of a polyester type condensation polymer which can be blow molded. The preferred types of materials for blow molded containers are, however, polyolefins, that is, homopolymers and copolymers of ethylene, propylene, 1-butene, 1-pentene, 4-methyl-1-pentene, 3-methyl-1-butene, 3,3-dimethyl-1-butene and the like.

Attempts to overcome the tendency of nonpolar organic fluids to diffuse through the walls of blow molded thermoplastic containers have included treating the surfaces of the containers both during and after the blow molding process, as well as the use of polymer blends.

One representative post-treatment method for providing a barrier layer on the surface of a polyolefin object and making blow molded polyolefin containers relatively impermeable to nonpolar solvents has been proposed by Joffre in U.S. Pat. No. 2,811,468. In this process, the internal surface of a blow molded bottle is fluorinated with pure fluorine or with a mixture of fluorine and air/nitrogen. The fluorinated containers thus produced have much better barrier properties toward hydrocarbon solvents then untreated containers. The barrier properties were determined by testing with allyl caproate, a volatile, highly odoriferous material. However, even accelerated testing requires a long period of time.

A more effective and economical way of obtaining blow molded containers, having enhanced barrier properties to hydrocarbon solvents, is proposed by Dixon et al. in U.S. Pat. No. 3,862,284. Dixon et al. teach that, in the blow molding of thermoplastic materials, 0.1-10% by volume of fluorine and 99.9-90% by volume of an inert gas are blended into a fluid medium before expanding the parison of the container to the contour of the mold. Containers produced by this process, using the AIROPAK ® system, have an interior surface which is extremely resistant to permeation by nonpolar organic solvents. See, for example, "Fluorination of Polyolefin Container During Blow Molding to Reduce Solvent Permeation, "*Plastics and Rubber Processing,* (March 1979), pages 10-16.

Another commercially available process for enhancing the barrier properties of blow-molded containers, known as the Dow sulfonation process, employs post-treatment of the container with a mixture of sulfur trioxide and nitrogen or dry air. This step is followed by treatment with ammonia and a dry diluent gas. This technique is discussed in the article, "Industrial Blow Molding: The Sleeping Giant Stirs," *Modern Plastics,* (November, 1977), pages 34-37.

It has also been proposed to improve the barrier properties of polyolefins by blending, for example, with polyamides. See, *Plastics World,* (July, 1983) at 33, 87.

A method for evaluation of solvent retention of surface fluorinated thermoplastics, as disclosed by Dixon et al. '284, is measuring gross loss of weight from toluene-containing bottles, kept at 100° F., for various periods of time. Another method comprises filling treated containers with motor oil, placing the filled bottles on filter paper and determining the time required for the oil to penetrate through the container to the filter paper.

Quality control in the manufacture of thermoplastic containers is accordingly limited by the lack of a rapid, inexpensive method to determine the efficacy of the surface treatment or polymer modification in decreasing solvent loss by permeation through the walls of the container. Any practically useful test for barrier properties must be rapid, permitting detection of variations in product properties very fast, so that immediate corrective action can be taken.

The tests described above are typical of methods which directly measure permeability of solvent through the walls of the container. Indirect methods, which measure properties other than permeability, but which can be related to permeability, can also be used.

One direct method for determining permeability is the pressure-accelerated permability method, in which a sample is cut from a treated container and mounted in a high pressure test cell. Liquid or gas is forced through the wall of the container by diffusion under high pressure. The material diffusing through the wall can be detected by physical or chemical means. This method is less than optimum because it is a destructive quality control test and because days or weeks may be required for determining the permeability of a particular sample.

Attempts have been made to measure permeability directly by exposing the inner surface of barrier-coated thermoplastic material, or a sample cut from the product, to a solution of an intensely colored or fluorescent dye, removing the solution after a preset period of time and determining the degree and depth of dye penetration into the walls of the product visually or instrumentally. This method is limited to products free of interfering dark colored and/or opaque pigments. correlate with those of colored or fluorescent dyes employed. Even when used for evaluation of specimens free from interfering additives, these tests are not highly reliable.

Available indirect tests for effectiveness of surface treatment include chemical or physical detection of the active component in the barrier layer, for example, fluorine in the AIROPAK ® system. When fluorine is used as the treating material, X-ray fluorescence, electron spectroscopy for chemical analysis (ESCA) or combustion, followed by chemical analysis, can be used. The ESCA technique employs low energy X-rays, which dislodge core electrons of molecules near the surface of the specimen being analyzed, and therefore permits specific analysis for elements at the surface of the sample.

Other techniques for determining surface properties of plastic materials include measurements of contact angle or total reflectance. These methods are often unreliable. Multiple internal reflectance (MIR), in which infrared data are analyzed by Fourier transform analysis, is considered more reliable, but is too complex to be employed for routine determination of surface properties.

Methods which test only small portions of the treated surface frequently fail to detect containers with unacceptable barrier properties, because a given surface may have been treated in a non-uniform fashion or because the polymer blend is not homogeneous. Optical and physical property determinations are also highly sensitive to contamination and, in some cases, difficult to correlate with barrier properties.

Evaluation of the permeability of a material toward carbon dioxide is often done by measuring decrease in pressure as a function of time. A commonly-utilized test requires study of 24 bottles for 24 weeks. Pressure loss through a film, employed in a gas permeation cell; analysis of organic vapors by gas chromatography; employing a Linde cell; and use of a cell in combination with an Oxtran ® oxygen analyzer (sold by Modern Controls) are alternative methods for evaluating permeability of films to gases and/or liquids. None of the foregoing methods permits the rapid accumulation of data, required for controlling a production line in a container plant.

Sorption of bromine from aqueous solutions by polyethylene has been studied by Allen et al., *Aust. J. Appl. Sci.*, vol. 12 (1961), pages 42-55. The reported mechanism of permeation of permanent gases through polyethylene is a combination of diffusion and solution.

It has been proposed by Morrisey et al. (U.S. Pat. No. 3,649,472) to test porosity of an electoplated article by determination of an electrolytic property, specifically corrosion potential.

Corrosion, measured as a function of time, is used by Just (U.S. Pat. No. 3,303,109) as a measure of diffusion profiles of semiconductor bodies.

Penetration of paper by a liquid has been assayed by a light-sensitive technique, as proposed by Berry et al. in U.S. Pat. No. 3,512,003.

The use of an electrical-colorimetric method to test the surface properties of a metal sample has been proposed by Alburger (U.S. Pat. No. 3,530,045).

It is accordingly the object of this invention to provide a rapid, economical, quantitative testing method, which correlates readily with surface permeability of thermoplastic containers, films or specimens.

DISCLOSURE OF INVENTION

In one aspect, this invention relates to a method for determining whether a thermoplastic article is measurably impermeable toward a fluid, and comprises the steps of:

(a) exposing a polymeric article to a permeant for a preselected period of time to permit the permeant to diffuse through the article;

(b) converting permeant which has diffused through the article to an ion by a chemical reaction and (c) measuring quantitatively the amount of thus-formed ion with an ion-specific electrode.

In another aspect, this invention relates to determination of permeability of a thermoplastic article to a fluid by the steps of:

(a) exposing the article to a permeant for a first preselected period of time;

(b) removing the article from contact with the permeant;

(c) treating the article with a chemical which will react with the permeant to form ions, following back-diffusion of the permeant to the surface of the article during a second preselected period of time; and (d) determining the amount of thus-formed ion quantitatively with an ion-specific electrode.

Permeation studies using containers filled at least partially with a typical permeant, bromine, were done by filling the containers and capping them with caps, impermeable to the permeant. Either metal or plastic caps, having polytetrafluoroethylene liners, can normally be used for this purpose. As shown in FIG. 1, the bottle containing permanent was placed inside a beaker containing a chemical, in this case, sodium formate solution, which will react with bromine permeant to produce bromide ions. The formate solution can be stirred and heated. Into the formate solution was placed an ion-specific electrode, specific for bromide ions, and a reference electrode.

Owing to the hazards associated with handling bromine, it will be understood that use of bromine as permeant in the method of this invention in a production facility will require provision for environmental safety, such as fume hoods, and that personnel carrying out the method of this invention will routinely wear proper eye and skin protection. It will further be understood that solutions of bromine, or other permeants, in aqueous or non-aqueous solvents, can be used. In the case of bromine, a minimum of 1% by weight of bromine is used. It is preferred to use more concentrated solutions, such as methanol or carbon tetrachloride solutions, containing at least 20% by weight of bromine. For these solvents, the upper limit on the amount of bromine is essentially pure bromine.

The conventional toluene permeation test, results of which are shown in FIG. 2, requires several days' testing before measurable loss of toluene was observed for treated bottles. In contrast, the permeability tests of this invention provide a significantly more rapid method of determining permeability than the toluene test.

In a representative embodiment, the method of this invention provides a simple and economical technique for determining parts per million of permeant, going through a polymeric article. Trace amounts of bromine, diffusing through the specimen initially, are converted to bromide ions by reaction with sodium formate:

$$Br_2 + HCOONa \rightarrow NaBr + HBr + CO_2.$$

In an aqueous solution, the product will be in ionic form. Specifically, $Na^+$, $H^+$ and $2Br^-$ would be produced by the foregoing reaction.

Utilization of a bromide-specific electrode is accordingly a simple way in which to measure indirectly the amount of bromine which had permeated the polymeric sample in a given period of time. The lower limit of $Br^-$ is limited only by the accuracy of calibration and/or the sensitivity of the electrode system.

It will be appreciated that it is conventional to determine the quality of a barrier by measuring the permeability constant of a selected permeant through the barrier. However, in order to measure the permeability constant, it is necessary to achieve a steady state of permeation. This could take several hours or several days.

A feature of this invention is that, rather than relying on the permeability constant to measure barrier quality, initial rapid permeation of a permeant is utilized. It is known that bromine permeates through polyethylene much more rapidly, by about two orders of magnitude, than does a typical organic solvent. In addition, any permeant passing through the polymeric specimen is chemically reacted to form ions. Therefore, the driving force for permeation is maintained because the concentration of permeant never builds up on the non-permeant side of the specimen. Accordingly, measurement of the time for permeation producing only a few ppm of bromine gives a valid measurement of relative barrier qualities.

As shown in FIG. 3, again using bromine as a typical permeant, permeable air-blown high density polyethylene (HDPE) bottles, charged with varying amounts of bromine, showed similar permeation characteristics, except that the bottle containing the larger charge of bromine was correspondingly faster in bromide production than the bottle containing the lesser charge of bromine, as a function of time. However, the difference in time required to reach a given amount of bromide ion was constant, of the order of 8 minutes. This difference in penetration rates was judged to be inconsequential, in view of the nearly four-fold difference in bromine charged.

It is thought that the difference in time for reaching a given bromide concentration can be explained by considering the relative surface areas, available for permeation by liquid and by vapor. The concentration of bromine in the liquid state is unity (1 g/g), whereas the partial pressure of bromine vapor is 0.26 (vapor pressure of $Br_2$ at 25° C. is about 200 mm Hg, whereas the pressure inside the bottle is 760 mm Hg). According to Fick's first law

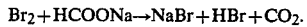

$$F = -D \cdot [(\Delta C / \Delta x)]$$

wherein F=flux of permeant across a membrane, D=diffusion coefficient, C=concentration of the permeant and x=space coordinate normal to the section.

It follows that flux is directly proportional to the concentration gradient. In the vapor phase, the concentration gradient is far less than in the liquid state. Therefore, the permeation rate will be higher when the amount of liquid permeant is increased.

Nevertheless, although the rate of permeation increases as the amount of permeant is increased, the increase in permeation rate is not proportionally higher. Accordingly, it is feasible to adjust the amount of bromine or other permeant and the period of time for permeation, to achieve a reasonably rapid test protocol.

The effect of temperature on behavior of a typical permeant, bromine, was evaluated at room temperature and at 40° C. using bottles blown with nitrogen (controls) and with varying amounts of fluorine/nitrogen. Results of these studies are shown in FIG. 4.

It was found that increasing the temperature for testing increases the permeation rate substantially. Also apparent is the superior barrier qualities of bottles, blown with 0.3% fluorine/nitrogen. This finding is consistent with other data, indicating the superiority of bottles, blown with 0.3% fluorine. However, even bottles blown with 0.3% fluorine are more permeable at 40° C., than those blown with nitrogen and treated with permeant at 25° C.

Accordingly, it is believed that testing at temperatures near ambient provide the most reliable conditions. It is therefore preferred to carry out permeation testing at 10°–40° C., at about atmospheric pressure, with a permeation time of 0.5–6 hr.

In the back-diffusion method of this invention, the following steps are required:
  (a) permeation of a permeant into the article for x minutes;
  (b) removal of excess permeant;
  (c) exposure of the sample to an ion-producing reagent and
  (e) measurement of the ions produced after z minutes.

It will be understood that, when the article being studied is a bottle or other type of container, the back diffusion method is non-destructive. Accordingly, bromine or other permeant is charged to the continer and, at the preset time, poured out. Following the optional rinsing step, ion-producing reagent is charged to the container for the second preset period of time. After the ion-producing reagent is removed from the container to another vessel, the amount of ions produced is determined as above.

Back-diffusion of bromine for a variety of HDPE bottles is shown in FIG. 5 as a function of back-diffusion time. As was the case for direct permeation, bottles known to have poor barriers for organic solvents showed large amounts of back-diffused bromide ion.

Bottles blown with air or with nitrogen showed extremely poor barrier behavior. Slightly better barrier behavior was observed for bottles blown with 0.1% fluorine in nitrogen (by volume) at 60 and 80 psig. Better results were apparent with bottles blown with 0.1% fluorine by volume in nitrogen at 100 psig and 0.3% fluorine at 80 psig. These results are consistent with those of other studies. The best results were observed for bottles blown with 1.45% and 2.0% of fluorine in nitrogen. Therefore, back-diffusion results are representative of bromine permeation and of permeation of typical organic solvents. More particularly, back-diffusion test results simulate bulk permeation of toluene through similarly treated HDPE bottles.

It is believed that in well-fluorinated containers, a significant amount of hydrogen, as from polyethylene, is replaced by fluorine up to a depth of about 400-500 Å. In poorly treated containers, the amount of hydrogen displacement is significantly less, as is the depth of fluorine penetration. It is thought that the fluorine incorporated near the surface of the polymeric specimen not only affects surface energy and solubility characteristics, but also produces crosslinking and provides steric hindrance against permeation. It is therefore proposed that a non-fluorinated, or otherwise unmodified surface, can be wetted and solvated rather readily by bromine or other suitable permeant. These initial steps of the permeation process occur rather rapidly. When the driving force for permeation, permeant outside the wetted surface, is removed, the permeated permeant is though to back-diffuse quickly. However, when barrier characteristics have been successfully imparted to the surface, the surface energy will be changed and the permeant will diffuse in rather slowly. Accordingly, upon removal of the permeant, less permeant is available for back diffusion. Therefore, a poorly-treated surface barrier will back-diffuse relatively large amounts of bromine or other permeant, whereas a good barrier will not.

In utilizing bromine as the permeant, it is preferred that the initial period of exposure to bromine be 1-30 minutes. Exposures of about 10 minutes are generally quite satisfactory.

Although washing permeant from the article is not a critical aspect of this invention, it is preferred that the permeant be washed away from the article being tested before the article is exposed to the ion-producing reagent. However, the solvent, selected for washing away permeant from the specimen, can affect differentiation obtained among good and poor barriers. Both methylene chloride and methanol are good solvents for bromine. In the case of nitrogen-blown bottles, back diffusion was 900 ppm of bromide ion for bottles washed with methanol and 350 ppm for bottles washed with methylene chloride, other parameters being kept constant. For bottles blown with 2.0% fluorine, back-diffusion was 70 and 100 ppm, when the bottles were rinsed with methylene chloride and methanol, respectively. Therefore, although both solvents are preferred for removing bromine permeant, methanol permits slightly better differentiation between surface characteristics.

It is postulated that, because the solubility parameter of bromine ($\sim$11) is much closer to that of methylene chloride ($\sim$10) than to that of methanol ($\sim$14), bromine has a greater tendency to back-diffuse during a methylene chloride rinse. It is also known that fluorine-treated containers are more permeable to methylene chloride than to methanol, possibly because methylene chloride can plasticize a treated HDPE wall.

Solvent rinse time also affects the amount of bromide or other ion, ultimately detected with the ion-specific electrode. In a representative test, nitrogen blown bottles were rinsed with methylene chloride for 1 and 3 min, under otherwise identical test conditions. Bromide ion concentrations were 580 and 425 ppm, respectively.

Retention time for the reagent, reacting with the permeant to form ions, also influences the amount of ion measured. Air blown bottles, treated with sodium formate solution for 1 and 2 minutes, respectively, registered bromide ion concentrations of 560 and 740 ppm, respectively. Bottles blown with 2% fluorine, under identical test conditions, gave bromide ion concentrations of 70 and 102 ppm after 1 and 2 minutes' treatment with sodium formate solution.

However, rapid rinsing, of the order of about 10-15 sec, with solvent for the permeant will be preferred. Increasing back-diffusion time has also been found to improve differentiation among treated specimens. Although the time for back-diffusion is preferably 1-30 minutes, back-diffusion times in excess of about 2 minutes will normally provide adequate differentiation. It follows that the technique of this invention permits rapid determination of barrier properties of plastic materials and that meaningful results can usually be obtained within 15 minutes at most.

Although it would appear that residual permanent in contact with the polymer specimen after rinsing could give misleading results, it was found, as shown in FIG. 6, that adhering permeant produces a curve, shown at (3-3), which is very similar to that of a good barrier (1-1). It is also seen from FIG. 6 that good and poor barriers have completely different properties, as shown at (1-1) and (2-2).

Permeability measurements proposed in accordance with the practice of this invention can therefore be used as a rapid test method for representative containers taken from a line of blow molding machines to permit monitoring product quality. It follows that adjustments in the conditions employed in the molding machines can be made rapidly, so as to preclude unnecessarily high loss of materials, should it become apparent that defective, i.e. permeable, containers are being produced by the machines on the line.

In the utilization of this invention, most meaningful results will be obtained if the yield of ions formed, as a function of time, from permeated permeant is correlated with long-term permeability of the container to a selected nonpolar fluid by comparison with a calibration curve, specific for the fluid. The calibration curve will also usually be specific for other parameters, such as wall thickness of the container and temperature of the test. It is preferred that the selected volatile non-polar fluid be toluene or gasoline.

In the specification and claims, "article" means film, plaque, sample and specimen, which are to be considered as interchangeable and are intended to include bottles, drums or tanks as well as sections cut out of such containers. In tests carried out to determine barrier properties of films or cut out of other articles, an impermeable test cell, sealed by a film, plaque or cut out of material being tested, can be used. If bromine is to be the permeant, the test cell can be glass or polytetrafluoroethylene and the gaskets and other parts of polytetrafluoroethylene.

Polymers which can be evaluated by the method set forth include phenolics, aminoplastics, epoxy resins, polyesters, silicones, polyolefins, polystyrene, polyvinyl plastics, fluorocarbon plastics, polycarbonates, polyamides, polyacetals, polyacrylates, polyphenylene oxides, polysulfones, polyurethanes and cellulosics, including homopolymers, copolymers, grafted copolymers and blends of any of the foregoing.

It is contemplated that the simple diffusion test of this invention will distinguish among the foregoing types of polymers, whether subjected to melt fluorination, post-fluorination, sulfonation, blending, co-extrusion, orientation, cross-linking or lamination. However, the back-diffusion test of this invention will be especially useful for determining the effect of surface modification, such as fluorination and sulfonation, as to level of treatment and uniformity.

Among permeants proposed for use in accordance with this method are acetic acid, ammonia, arsenious chloride, arsenious hydride, carbon dioxide, carbon disulfide, carbon monoxide, carbonyl chloride, carbon oxysulfide, carbon suboxide, chloric acid, chlorine, chlorosulfonic acid, chlorostannic acid, cyanogen, fluorine, hydrazine, hydrobromic acid, hydrochloric acid, hydrofluoric acid, hydrocyanic acid, hydroiodic acid, sulfur dioxide, hydrogen peroxide, nitrous oxide, nitric oxide, nitrogen trioxide, nitrogen dioxide, nitrogen oxybromide, nitrogen oxychloride, nitrosyl chloride, oxygen, ozone, phosphorous oxychloride, selenic acid, silicon trichloride, silicon tetrachloride, silicon tetrafluoride, silicon hydride, sodium chromate, sodium hydrosulfide, tin tetrachloride, sulfur monobromide, sulfur monochloride, sulfur dichloride, sulfur dioxide, sulfur trioxide, sulfuric acid, sulfuric oxybromide, sulfuric oxychloride, vandium tetrachloride, vanadyl trichloride, as well as readily ionizable organic acids and their halides, hydrolyzable organic halides and isocyanates and amines.

Ammonia diffusing through an article could be determined, using an electrode, specific for ammonium ion. In a similar fashion, hypochlorite could be determined using an electrode specific for chloride ion and iodine using an electrode specific for iodide.

Evaluation of diffusion of acetic acid or other organic acids, diffusing through an article, could be accomplished using a pH electrode.

Diffusion of oxygen through an article, e.g., film contemplated for packing meats, could be determined using the film to seal a test cell; converting diffused oxygen to hydroxide and measuring pH.

Determination of carbon dioxide can be made by converting carbon dioxide to carbonate ion, which is determined by an electrode specific therefor. Alternatively, carbonate could be measured indirectly, by difference, by precipitation of an insoluble carbonate, e.g. barium or calcium carbonate, and determination of residual barium or calcium ion concentrations. Another method for measuring carbon dioxide permeant is conversion to the bicarbonate, which could be measured by a pH electrode.

Preferred permeants are bromine, acetic acid, hypochlorous acid or hypochlorite, oxygen, carbon dioxide, ammonia or aqueous ammonia, carbon oxychloride and iodine. However, bromine is most preferred, whether pure or in solution in an organic solvent, such as methanol.

Chemical reagents which will convert permeant to ions include any material which will convert or hydrolyze the permeant to an ionic form, detectable by an ion-specific electrode. It is accordingly contemplated that electrodes specific for ammonium, hydrogen, bromide, cadmium, calcium, mercury, lead, silver, sodium, carbonate, chloride, iodide, fluoride, chlorine, cyanide, nitrate, nitrite, sulfide or other ions will be useable in the practice of this invention.

The specimens tested in accordance with this invention are preferably of polyolefin, more preferably of an ethylene polymer or copolymer.

BEST MODE FOR CARRYING OUT THE INVENTION

In most preferred aspects, the method of the invention will be done by the back-diffusion method.

In either case, a method will be preferred wherein the permeant is bromine and the electrode is specific for bromide ion. Most preferably, the bromine will be converted to bromide ion by reaction with formic acid or sodium formate. Preferably, the article being examined will be of an olefin polymer or copolymer, most preferably of polyethylene.

In the direct permeation testing, it will be preferred that the amount of bromide ion formed is correlated to long-term permeability of the polymeric article by comparison with a calibration curve, specific for a fluid of interest, and that the specimen is exposed to bromine at 10°–40° C. at about atmospheric pressure for 0.5–6 hr.

A similar back-diffusion assay will be preferred, wherein bromine is washed from the article with methanol or methylene chloride; wherein the polyethylene article is exposed to bromine from ambient temperature to about 50° C. at ambient pressure for 1–30 minutes and rinsed with methylene chloride or methanol wherein and the period of back-diffusion is 1–30 minutes.

Without further elaboration it is believed that one skilled in the art can, using the preceding description, utilize the present invention to its fullest extent. The following specific embodiments are, therfore, to be construed as merely illustrative and not limitative of the remainder of the disclosure in any way whatsoever. In the following Examples, the temperatures are set forth uncorrected in degrees Celsius. Unless otherwise, indicated, all parts and percentages are by weight.

EXAMPLE 1

Bottles (16-ounce size), blow molded from Marlex ® polyethylene (high load melt index=10) by the method of Dixon et al., '284, weighed about 30 grams and had a minimum wall thickness of about 0.025 inch. Samples obtained at various $N_2/F_2$ ratios (0.1–2.0% $F_2$ by volume) were tared, filled with toluene and reweighed. The bottles were placed in a constant temperature oven (50° C.) and weighed at intervals for 28 days. The oven was blanketed with nitrogen to prevent the gas composition within the oven from moving into the explosive limits for toluene. The project was carried out under a hood to prevent buildup of toluene fumes.

Percent weight loss of solvent after a given interval is:

$$\% \text{ loss} = \frac{[(Y - X) - (Z - X)]}{(Y - X)} \times 100\%$$

wherein X=tare weight of capped bottle, Y=initial weight (day 0) of capped, solvent-filled bottle and Z=weight of bottle on subsequent days.

The total loss over the selected testing period used Z, determined for the final day of that period. Permeation curves were obtained by plotting the total percentage weight loss against the running time of the testing period. The change in the rate of solvent weight loss was apparent from a change in the slope of the permeation curve.

Figure 2:
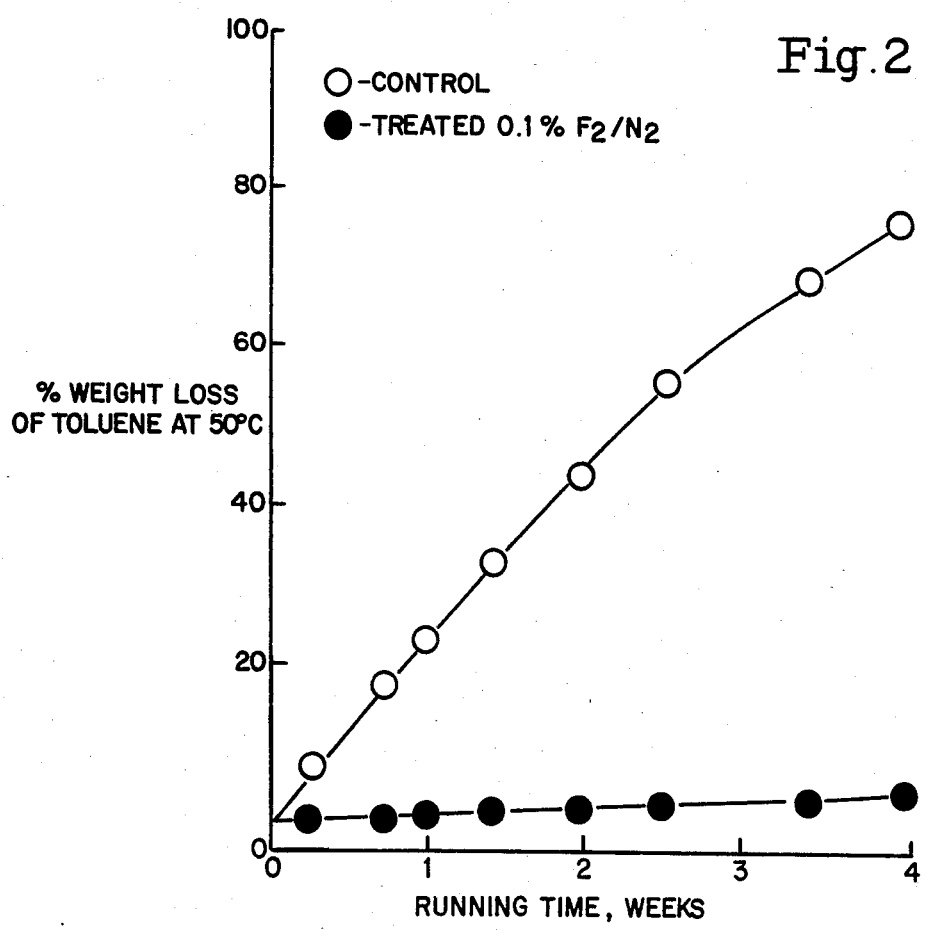
In FIG. 2 is shown a plot of loss of toluene through the walls of various polyethylene containers at 50° C. as a function of time.

As shown in FIG. 2, polyethylene bottles treated with 0.1% $F_2$ in $N_2$ displayed almost no loss of toluene at 50° C. during a month of testing, whereas significant loss of toluene from the control bottles was apparent within a day or so from the start of the experiment.

From data obtained by accelerated testing at 50° C., predictions as to weight loss on storage for extended periods, e.g., a year at room temperature (23° C.) have been made.

However, because a treated container (0.1% $F_2$ during blow molding) showed only 0.1% loss of toluene after seven days' testing, it is apparent that testing of treated containers by accelerated toluene loss, is not a practical way in which to carry out quality control.

EXAMPLE 2

Polyethylene (HDPE, 16-ounce size) bottles, blown at 80 psig, and treated with air or nitrogen or with fluorine either during expansion of the parison during blow molding or afterwards, were filled at least partially with bromine and capped with a cap having a polytetrafluoroethylene liner to prevent degradation of the cap. Handling of bromine was done under an exhaust hood by personnel with adequate skin and eye protection.

Figure 1:
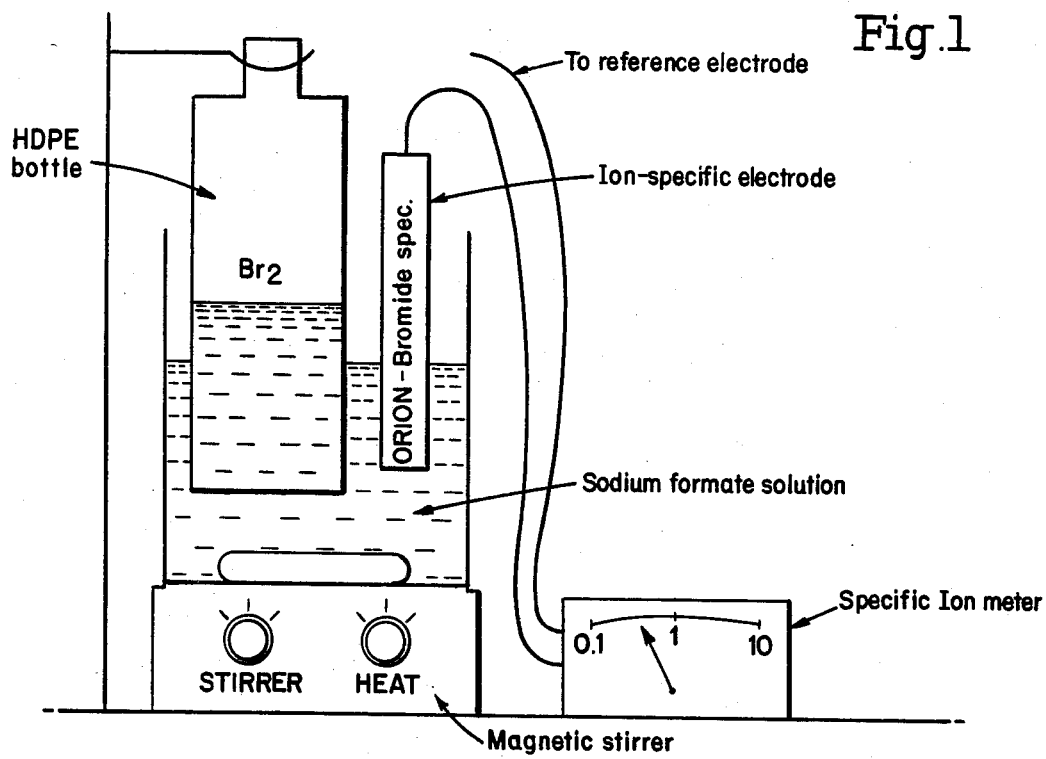
In FIG. 1 is shown an apparatus for use in carrying out the invention.

In each experiment, a 600-ml glass beaker was filled with 1% aqueous sodium formate solution. Into this beaker was placed a bromine-filled bottle, as shown in FIG. 1. The sodium formate was maintained at the selected temperature and stirred constantly with a magnetic stirrer.

A bromide-specific electrode and a reference electrode (Orion K-5710-01) were placed in the sodium formate solution to permit measurement of bromide ion as a function of time. The meter used could be calibrated to read concentrations without two orders of magnitude.

The ion-specific meter employed was a pH/specific ion meter (Orion, Model No. 407 A/L), equipped with a bromide specific electrode and a single-junction reference electrode. The bromide electrode consisted of silver bromide/silver sufide membranes, bonded into the tip of an epoxy electrode body. When the membrane is in contact with a solution, containing bromide ions, silver ions dissolve from the surface of the electrode membrane, so that the electrode develops a potential due to silver ion concentration. Silver ion concentration is, in turn, determined by bromide ion concentration of the sample. The resulting potential is measured against a constant reference potential provided by the reference junction electrode. The measured potential corresponding to the level of bromide ion in solution is described by the Nernst equation.

EXAMPLE 3

The effect of amount of bromine charged to 16-ounce HDPE bottles, 17 cm in height and 6 cm inner diameter, was determined at room temperature. One bottle contained 138 g of bromine and a second bottle 500 g. The height of bromine in the bottles was 1.6 cm and 5.7 cm, respectively. The ion-specific meter was calibrated to read between 1 and 100 ppm of bromide ion.

Figure 3:
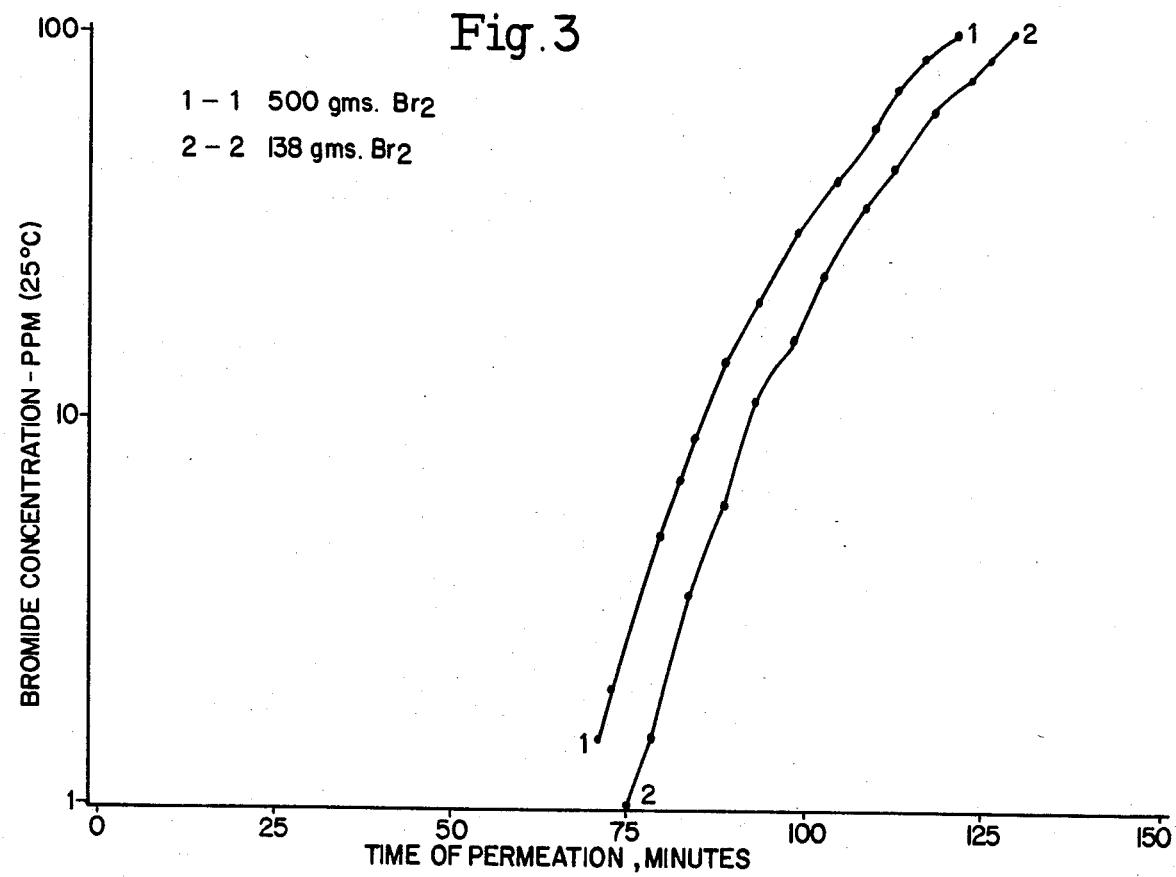
In FIG. 3 is shown the effect of amount of bromine charged to air-blown bottles on permeation as a function of time.

As shown in FIG. 3, the initial time difference in reaching a given bromide concentration was large, but soon decreased to a constant time (about 8 min).

These results show that partially filled containers can be used in accordance with this invention as long as the procedure is standardized to provide for the same extent of filling during a series of tests.

EXAMPLE 4

The effect of treatment on bromine permeation was demonstrated in an experiment, otherwise as in Example 2, using bottles treated in various ways. The ion-specific meter was calibrated to read between 10 and 1000 ppm of bromide.

Figure 4:
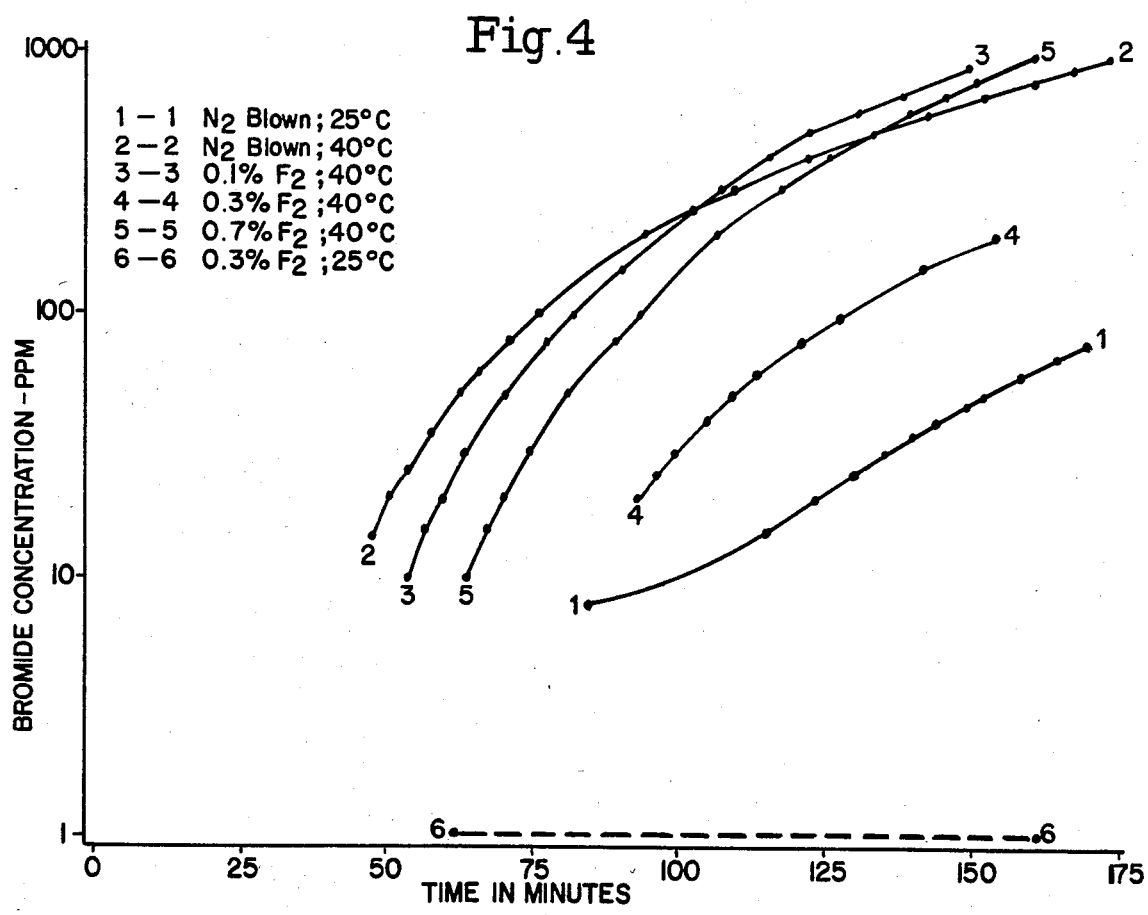
In FIG. 4 is given the relationship between temperature and time, as affecting bromine permeation through bottles treated in varying ways.

As shown in FIG. 4, increasing the temperature generally also increased the amount of permeation. However, one bottle, blown with 0.3% fluorine and tested at 25° C. did not show any permeation at all after 3 hr, at which time the experiment was terminated.

EXAMPLE 5

Back-diffusion testing was done using 16-oz HDPE bottles, treated in various ways. After bromine had been left in the bottle for a specified period of time, bromine was poured out. The bottle was washed with a solvent, such as methylene chloride or methanol, for a selected period of time. The bromine-containing solvent was poured out of the bottle, which was then filled with 1% aqueous sodium formate solution. The sodium formate solution reacted with any bromine, which back-diffused from the wall of the bottle. At the end of the test period selected, the formate solution was poured into a vessel containing the ion-specific meter. Bromide ion concentration of this solution was determined as in Example 2.

In typical experiments, a pair of air-blown bottles treated with bromine for 1 min had bromide ion concentrations of 470 and 580 ppM, following back-diffusion. A bottle exposed to bromine for 3 min had back diffusion of 970 ppm.

EXAMPLE 6

The top halves of 16-oz HPDE bottles were cut off and about 200 ml of bromine was poured into each of the bottom halves. The bottoms were covered and kept still, so that bromine could penetrate into a fixed surface area. At the end of ten minutes, bromine was poured out and each container was rinsed with 100 ml of methanol. Then, 100 ml of 1% sodium formate solution was added to each container bottom. This solution was stirred with a magnetic stirrer while bromide ion concentration as a function of time was determined using a bromide-specific electrode.

Figure 5:
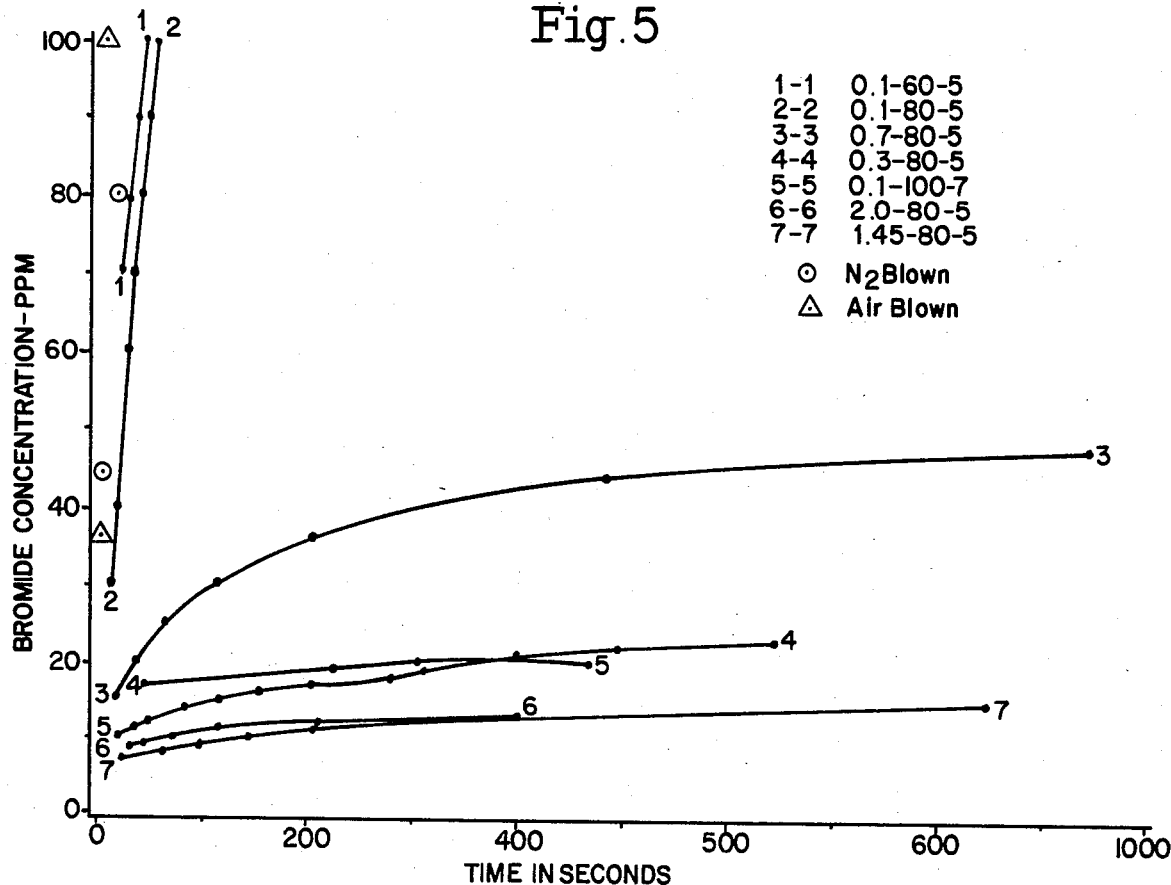
In FIG. 5 is shown the relationship among surface treatment and bromine back-diffusion, as a function of time.
Figure 6:
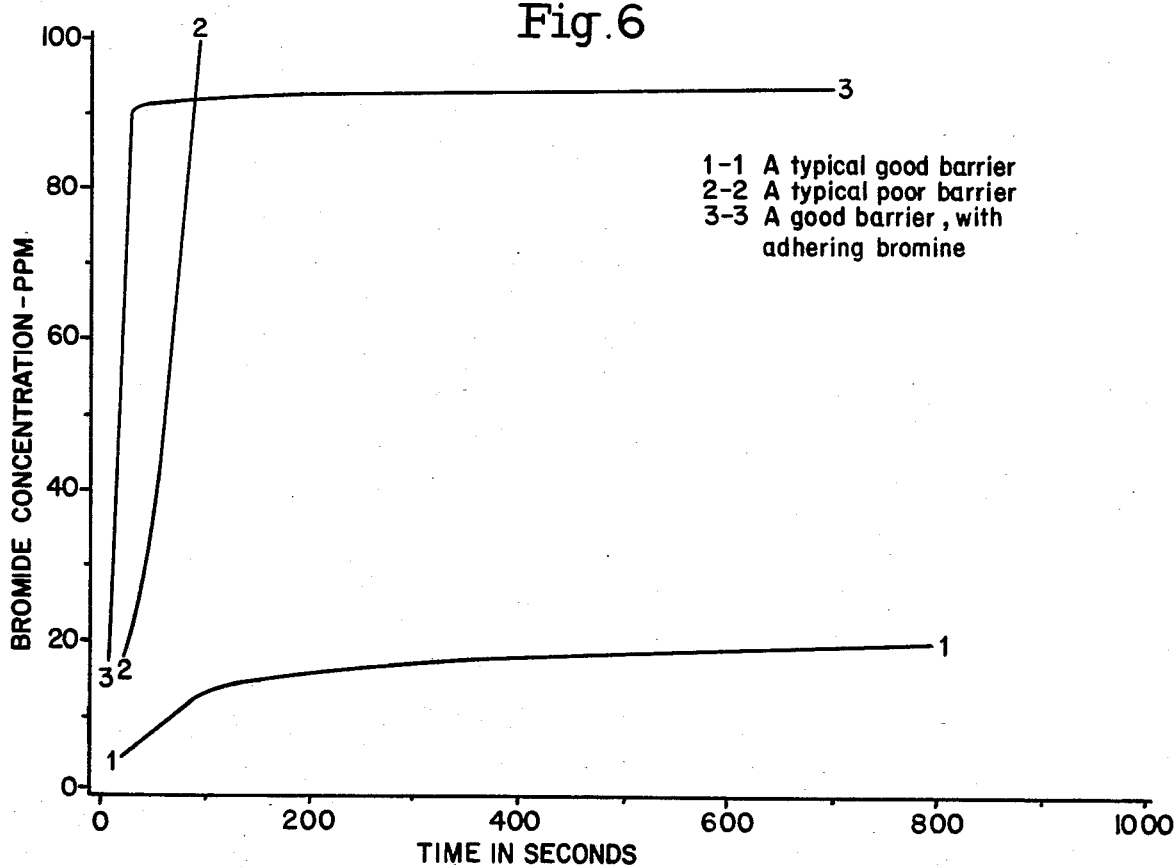
In FIG. 6 is represented the effect of permeant carry-over on back-diffusion results.

The results obtained are shown in FIG. 5 and show that back-diffusion of bromine is a valid measure of barrier properties. In FIG. 5, "0.1-60-5" means a HDPE bottle was blown with 0.1% by volume of fluorine (balance nitrogen) at a blow pressure of 60 psig over a 5 sec cycle.

EXAMPLE 7

The effect of treatment on bromine permeation was shown in an experiment, otherwise as in Example 2, using a pair of bottles, one blown with nitrogen and the other with 0.3% by volume of fluorine (balance nitrogen). Each bottle was charged with 50 g of bromine. The ion-specific electrode was calibrated to read between 10 and 1000 ppm of bromine. At the end of the 95 minute testing period, bomide-ion concentrations, produced by diffusion from the two bottles, were 200 and 20 ppm, respectively.

The foregoing is a representative test protocol for use in accordance with this invention.

EXAMPLE 8

The effect of treatment on bromine back-diffusion was demonstrated in an experiment, using two 16-oz HDPE bottles, one of which was blown with nitrogen and the other blown with 0.5% by volume of fluorine in nitrogen. The test was as in Example 6, using 50 g charges of bromine in each case. At the end of one minute, bromine was poured from the bottle sections and each section was rinsed with a 100-ml portion of methanol. Then, 100 ml of 1% sodium formate solution was poured into each bottle section. The solution with stirred with a magnetic stirrer while bromide-ion concentration was measured with an ion-specific meter, calibrated to read between 1 and 100 ppm of bromide.

At the end of thirty seconds, the container section, blown with 0.5% of fluorine had permitted back diffusion of 11 ppm of bromide. At the end of 90 sec, the nitrogen blown specimen had permitted back-diffusion of more than 100 ppm of bromide.

This experiment is typical of test protocols for employing the back-diffusion method of this invention.

EXAMPLE 9

Glass test cells, fitted with plate seal for material being tested and provided with polytetrafluoroethylene gaskets, are filled with bromine to evaluate the permeability of cut outs from a polyethylene fuel tank treated with sulfur trioxide and of untreated polyethylene sheet. Permeation is determined as in Examples 2 and 5.

EXAMPLE 10

(a) Bromine (6.0 g) was dissolved in 194.0 g of distilled water to produce a nearly-saturated solution. Each of two 16-oz HDPE bottles, one blown with air and the other with 0.3 $F_2$ by volume in $N_2$, was charged with 100 g of the bromine water solution. Each of the bottles was weighed.

After 24 hours' storage at room temperature, the bottles were reweighed. The air-blown bottle had lost 0.12 g of bromine, whereas the weight of the fluorine-blown bottle was unchanged.

(b) Bromine (100 g) was dissolved in 200 g of methanol. Each of two 16-oz HDPE bottles, one blown with air and the other with 0.3% by volume of $F_2$ in $N_2$, was charged with 150 ml of this solution. The bottles were weighed and kept at room temperature.

At the end of 24 hours' storage, each of the bottles was reweighed. The bottle blown with fluorine showed no measurable loss of weight, whereas the bottle blown with air had lost more than 1.5 g, most of which was attributed to diffusion of bromine out of the container.

(c) Similar results are obtained, using a solution of bromine in carbon tetrachloride.

These experiments show that bromine, dissolved in various solvents, can be used to determine barrier properties of thermoplastic materials. The amount of bromine lost can be determined by conversion to bromide ions and measurement of the bromide ions with an ion-specific electrode.

EXAMPLE 11

(a) A polyethylene terephthalate bottle is charged with carbonated water and placed in a water bath containing a bicarbonate-producing reagent, in a glove box. The production of bicarbonate ion is followed using an electrode specific for bicarbonate ions.

(b) Household ammonia solution is charged to a polyethylene bottle and placed in a container of ammonium-ion producing reagent. The rate of production of ammonium ions is followed with an electrode system, specific for ammonium ions.

(c) Sodium hypochlorite solution (household bleach) is charged to a polyethylene container, placed in a vessel containing a chloride-producing reagent. The production of chloride ions is monitored using an electrode system, specific for chloride ions.

(d) Transparent plastic wrapping material is used in a test cell, charged with oxygen, and placed in a vessel containing a reagent, which will convert oxygen to hydroxide ions. The experiment is carried out in an inert atmosphere in a glove box. Production of hydroxide ions is followed using a pH electrode.

(e) Tincture of iodine is charged to a polyethylene container, which is immersed in sodium formate solution. The production of iodide ions in this solution is followed using an iodide-sensitive electrode.

From the foregoing, it is apparent that a variety of plastic substrates can be tested for determination of permeability to numerous materials.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A method for determining the permeability of a polymeric article to a nonpolar fluid comprising the steps of:
    (a) allowing bromine to diffuse through a polymeric article for a preselected period of time of 0.5–6 hours at 10°–40° C.;
    (b) converting bromine which has diffused through the polymeric article to bromide ion by a chemical reaction;
    (c) quantitatively measuring the amount of bromide ion formed in step (b) with a bromide ion-specific electrode as a measure of the permeability of the polymeric article to bromine; and (d) determining the permeability of the polymeric article to a nonpolar fluid by correlating the bromine permeability of the article to long-term permeability of the article to the nonpolar fluid by comparison with a calibration curve specific for the nonpolar fluid.

2. The method of claim 1, wherein bromine which has diffused through the polymeric article is converted to bromide ion by reaction with formic acid or sodium formate.

3. The method of claim 1, wherein the article is a bottle, filled at least partially with bromine and placed in a solution of a chemical which will convert bromine which has diffused through the bottle, to bromide ion.

4. The method of claim 1, wherein the polymeric article is of an olefin polymer or copolymer.

5. The method of claim 1, wherein the polymeric article is of polyethylene.

6. The method of claim 1, wherein the polymeric article is of polyethylene and bromine which has diffused through the article is converted to bromide ion by reaction with sodium formate or formic acid.

7. The method of claim 1 wherein the polymeric article is of a thermoplastic which has been fluorinated.

* * * * *